United States Patent [19]
DeBonville et al.

[11] Patent Number: 4,833,239

[45] Date of Patent: May 23, 1989

[54] METHOD FOR THE ISOLATION AND PURIFICATION OF DNA MOLECULES

[75] Inventors: David A. DeBonville, Cambridge; Gerard E. Riedel, Concord, both of Mass.

[73] Assignee: Genetics Institute, Inc., Cambridge, Mass.

[21] Appl. No.: 8,500

[22] Filed: Jan. 29, 1987

[51] Int. Cl.$^4$ .............................................. C07H 21/04
[52] U.S. Cl. .......................................... 536/27; 536/28; 536/29
[58] Field of Search .............................. 536/27, 28, 29

[56] References Cited
PUBLICATIONS

Blair et al., J. General Virology, vol. 64, pp. 2697–2715 (1983).
B. Salser et al., Biochim. Biophys. Acta, v. 378, pp. 22–34 (1975).
Alwine et al., pp. 220–242 in Methods in Enzymology, vol. 68, Edited by P. Wa, Academic Press, N.Y., N.Y., 1979.
Methods in Enzymology, vol. 65, pp. 404–411, 718–721, 1980.

*Primary Examiner*—Ronald W. Griffin
*Assistant Examiner*—L. Eric Crane
*Attorney, Agent, or Firm*—David L. Berstein; Bruce M. Eisen; Brian P. O'Shaughnessy

[57] ABSTRACT

A method for isolating and purifying nucleic acids from eukaryotic and prokaryotic cell cultures or viral cell cultures.

3 Claims, No Drawings

METHOD FOR THE ISOLATION AND PURIFICATION OF DNA MOLECULES

The present invention relates to a procedure for isolating and purifying double-stranded plasmid DNA or single-stranded bacteriophage DNA replicated in eukaryotic and prokaryotic cell and virus cultures in appropriate conditioned medium. This is a continuation-in-part of co-owned, co-pending United States patent application Ser. No. 908,413, filed Sept. 17, 1986.

BACKGROUND OF THE INVENTION

In recombinant DNA research, DNA molecules are commonly isolated from bacterial cell cultures and bacteriophage cultures. For example, double-stranded plasmid DNA is produced within and isolated from bacterial cells, e.g. *Escherichia coli*, that are cultured in liquid nutrient broth media. Bacteriophage M13 single-stranded template DNA is produced by the bacteriophage M13 propagated on an appropriate *E. coli* host. Template DNA is isolated from bacteriophage that have been released by host bacteria into a nutrient broth media. The isolation of these plasmid DNA or template DNA molecules enables the sequencing thereof, and the use of the molecules for diagnostic and other assays, for their assembly into genes encoding a polypeptide of interest or for their use as vectors to produce such polypeptides.

The procedure commonly used for the isolation of plasmid DNA from bacterial cultures is described in H. C. Birnboim and J. Doly, "A Rapid Alkaline Extraction Procedure for Screening Recombinant Plasmid DNA", *Nucleic Acids Res.*, 7:1513–1523 (1979). Template DNA is isolated in a similar manner. See, e.g., Leder et al, *Science*, 196:175 (1977). Briefly, the DNA is separated from contaminating proteinaceous material in the conditioned medium by lysis in the presence of lysozyme in a detergent and a salt solution. This lysis step is followed after an incubation step at a low temperature by extration or deproteinization with phenol or chloroform or a mixture thereof. The nucleic acids are then separated by precipitation from lipid and other protein constituents of the culture. These two steps—lysis and deproteinization—are separately performed because the reagents in the lysis steps are not miscible with the reagents involved in deproteinization. See, also, T. Maniatis et al, *Molecular Cloning-A Laboratory Manual,* Cold Spring Harbor Laboratory (1982) for the specific steps of the presently-used procedure.

Due to the frequency with which these DNA isolating and purifying steps are employed and the researcher time which is consumed in performing the Maniatis et al steps, there is a need in the art of recombinant DNA research for more efficient methods of DNA isolation.

SUMMARY OF THE INVENTION

The present invention provides a method for the isolation of DNA from contaminating proteinaceous and lipid material in a culture medium. This method is both efficient and effective in obtaining purified DNA molecules and fragments and has significant advantages over presently employed procedures.

The steps of the method of the present invention for isolating and purifying DNA molecules include the following steps common for both plasmid DNA and template DNA:

First, the cells in the culture are concentrated apart from major contaminants in the media by centrifugation. When employing this method for the isolation of template DNA, the bacteriophage can be separated from host bacterial cells by low speed centrifugation, after which the bacterial cells are pelleted while the bacteriophage remain in the liquid media. Another alternative is to isolate both plasmid DNA from the bacterial host cells and template DNA from the bacteriophage in the liquid media by concentrating the bacteriophage with an additional centrifugation step.

Second, the cells are lysed in the absence of lysozyme and deproteinated at room temperature (or ambient temperature) as follows: The cells are gently vortexed in an isotonic buffer. One desirable buffer solution contains glucose, ethylene-diaminetetraacetic acid [EDTA] and Tris.Cl. After the first vortexing, a salt and detergent solution (desirably sodium hydroxide and sodium dodecyl sulfate [SDS]) is added to the buffer. This mixture is vortexed, and followed by the addition of the novel lysis and deproteinization reagent composition described and claimed in U.S. patent application Ser. No. 908,413, the disclosure of which is incorporated by reference herein i.e. a stable, single-phase aqueous composition including between 1.6 to about 3.2M potassium acetate, between about 5% to about 15% phenol by weight, between about 5% to about 15% by weight chloroform and glacial acetic acid in an amount such that the weight ratio of potassium acetate to acetic acid is 3:2. A third vortexing completes this simultaneous lysis and deproteinization step. Selection of the particular isotonic buffer and the salt and detergent solution involve conventional choices for one of skill in this art.

Third, the cellular debris is eliminated from the solution of the second step by centrifugation.

Fourth, the plasmid or template DNA is extracted by precipitation in an alcohol solution onto a suitable filter. A suitable filter for this purpose may be a cellulose acetate or nylon filter having a pore size of approximately 0.8 microns. Other such filters with different pore sizes may also be employed in this step.

Fifth, the precipitated DNA is bound to the filter by centrifugation at room temperature.

Sixth, the bound DNA is repeatedly washed to remove contaminants which otherwise might be co-purified with the DNA. The washing steps can be preformed with a lower alkyl alcohol, such as ethanol, which passes through the filter, removing contaminants but leaving the DNA on the filter.

Seventh, the bound, washed DNA is released from the filter by incubation at room temperature in a low ionic strength buffer. Such a buffer may include RNase, Tris.Cl and EDTA. Other buffers are well known to those skilled in the art of DNA isolation techniques.

This method employs reagents stable at room temperature, thereby permitting a single procedure to be effective to isolate and purify both single-stranded template DNA and double-stranded plasmid DNA. The present method also allows combination of the two steps of prior isolation techniques and thus simplifies the isolation procedure. Unexpectedly the method of the invention results in an increased yield of DNA molecule isolation over the prior art procedures and produces molecules of equal or greater purity. The absence of lysozyme from the procedure contributes to these advantages because that enzyme is effected by temperature, the genotype of the bacterial cell and the time it is allowed access to the cells. Unlike the prior art methods, the method of this invention employs reagents stable at room temperature and requires no cooling steps. Thus, it is susceptible to automated as well as manual performance. When automated, the procedure provides an increased time savings by freeing the researcher for other work.

DETAILED DESCRIPTION OF THE INVENTION

The method of the present invention fulfills a need in the field of recombinant DNA research by providing an efficient, and automatable procedure for the isolation and purification of single-stranded template DNA and double-stranded plasmid DNA.

The first step involves concentrating the cell culture by centrifugation. While the rate and time of centrifugation may be adjusted by one skilled in the art to account for the amount of culture media employed, a desirable rate of centrifugation is approximately 3000 rpm for approximately 10 minutes.

The lysis and deproteinization step involves sequential vortexing of the cell pellet in an isotonic buffer. One desirable isotonic buffer includes approximately 50 mM glucose, approximately 10 mM EDTA and approximately 10 mM Tris.Cl at a pH of approximately 7.5. Following one vortexing in this buffer at room temperature, a salt(e.g., 0.2N NaOH) and a detergent (e.g., approximately 1% SDS) are added with vortexing. The lysis and deproteinization reagent of Ser. No. 908,403 is then added, and upon vortexing, the plasmid or template DNA is lysed and deproteinized in solution.

Like the initial centrifugation, the rate and time of the third step centrifugation can be selected by one skilled in the art but is preferably approximately 3000 rpm for 10 minutes.

The fourth extraction step involves precipitating the DNA onto a filter. One presently preferable suitable filter is a nitrocellulose filter with approximately 0.8 micron pores. One example of such a filter which is additionally adaptable to an automated system is present in a Centrex TM tube [Schliecher & Schuell], having a 5 ml receiver tube. Alternative filters suitable for this step, e.g., nylon and the like, may be selected by one skilled in the art. The alcohol solution which is used to precipitate the DNA is preferably isopropanol, but may also be another lower alkyl alcohol such as 100% ethanol.

For the fifth step, centrifugation at a rate of approximately 3000 rpm for 4 minutes has been found sufficient to bind the DNA to a nitrocellulose filter. One skilled in the art could easily determine appropriate centrifugation parameters for other kinds of filters.

The repetitive washings of the sixth step of the method of the invention may be performed with a lower alkyl alcohol, preferably 70% ethanol. The number of washings sufficient to remove the contaminants can range from 1 to about 6; however, three washings is generally preferable.

Finally, the elution step to remove the DNA from the filter involves allowing the filter to stand at room temperature for approximately 30 minutes in a low ionic strength buffer. A presently preferable solution contains approximately 10 mM Tris-Cl at pH 8.0, approximately 1 mM EDTA and approximately 20 mg/ml RnaseA. The elution is followed by another centrifugation, which elutes DNA in this procedure at a rate of approximately 3000 rpm for 4 minutes. One of skill in the art may select another rate and time, if desirable.

The method of the present invention is capable of replacing a variety of standard DNA isolation procedures, including the isolation of DNA from tissue sources, e.g. eukaryotic cells as well as from prokaryotic cells.

The following examples illustrate presently preferred and automated embodiments of the present invention.

EXAMPLE I

Preparation of the Reagent Composition

The reagent composition described in copending application Ser. No. 908,413 and employed in the present invention is prepared as follows:

In a first solution, 48 mls 5M potassium acetate is mixed with 32 mls glacial acetic acid (a 3:2 weight ratio of the potassium acetate to acetic acid in this solution is preferred). A second solution is formed by adding in the following order: 9.9 mls phenol, 0.1% by weight 8-hydroxyquinoline, 9.9 mls chloroform, and 0.2 mls isoamyl alcohol. These two solutions are mixed together, thereby forming a stable single phase composition of pH 8.

EXAMPLE II

Plasmid DNA Isolation from Bacterial Cells

One embodiment of the method of the present invention involves plasmid DNA isolation from bacterial cell culture, which may be performed as follows: 5 mls of SOBM medium [Maniatis et al, supra p. 69]are inoculated with *E. coli* JM101 bacterial cells and M13mp19 bacteriophage and incubated overnight at 37° C. Cells are concentrated by centrifugation at a rate of 3000 rpm for ten minutes. After the medimm is poured off, the resulting pellet is resuspended in 0.3 mls of 50 mM glucose, lOmM ethylenediamine-tetraacetic acid (EDTA), and 10 mM Tris-Cl at pH 7.5 and vortexed for two minutes at room temperature. Immediately following the vortex step, 0.6 mls of 0.2N NaOH and 1% SDS is added and the solution vortexed gently at room temperature for 15 seconds, incubated for 30 seconds and vortexed gently again for 15 seconds.

To this solution, 0.54 mls of the composition of Example I is added. This mixture is gently vortexed for 15 seconds, incubated for 30 seconds, and vortexed again for 15 seconds, and then centrifuged for 15 minutes at 3000 rpm.

The resulting supernatant is transferred to a test tube having a 0.8 micron pore size cellulose acetate filter and a 5 ml receiver tube [Schliecher and Schuell]. 1.3 mls isopropanol is added to the tube and it is vortexed gently, followed by a 2 minute room temperature incubation. To bind the DNA to the filter, the contents of the tube are centrifuged for 4 minutes at 3000 rpm at room temperature. While the DNA is on the filter, 0.5 mls of 70% ethanol is added to the tube and centrifuged again for two minutes. This step is repeated three more times to insure complete removal of contaminants.

The receiver tube is then removed and replaced with a 1.5 ml, capless Eppendorf tube. 0.1 ml of a reagent solution containing 10 mM Tris-Cl at pH 8.0, 1 mM EDTA and 20 ugs/ml RNase A is added to the tube and incubated for 30 minutes at room temperature to allow the DNA to be released from the filter. The tube and its contents are then centrifuged for four minutes at 3000 rpm at room temperature.

10 ul of the resulting solution is placed in a new Eppendorf tube. 1.2 ul of 10X EcoRI buffer [New England Biolabs] is added with 1 unit of EcoRI restriction enzyme, and the resulting solution incubated for 2 hours at 37° C. The solution containing DNA fragments is analyzed by gel electrophoresis, producing linearized double-stranded plasmid DNA of 7.2 kb.

When the procedure described in Maniatis et al was applied to purify the same culture, the electrophoretic gel data produced the same results as did the above procedure employing the composition of the present invention. However, the time savings caused by use of the composition of the present invention in the automated procedure was approximately 10–15 percent. Additionally, in both the manual and automated DNA plasmid isolation procedures, use of the composition of the present invention resulted in significantly higher yields of the isolated DNA fragments.

EXAMPLE III

Template DNA Isolation from Bacteriophage M13

Another embodiment of the claimed method involves isolating single-stranded template DNA. This procedure is exemplified as follows: The culture employed in Example II is subjected to the same low speed centrifugation step. Thereafter, the liquid media which contains the bacteriophage is transferred to a new tube containing 2 mls of 1.5M NaCl in polyethylene glycol [PEG, molecular weight of 8,000]. The pellet containing the bacterial cells is not used in this procedure. The two solutions are mixed in the tube by repeated pipetting motion and allowed to sit at room temperature (e.g., ambient temperature) for at least 30 minutes.

The bacteriophage are then separated from the solutions by low speed centrifugation [3000 rpm] for 1 minutes, to enable them to be pelleted to the bottom of the tube. The supernatant is now discarded. The bacteriophage are "lysed" by first vortexing in a 0.9 ml solution of glucose, EDTA and Tris-Cl; followed by the addition of 0.7 mls of the novel reagent of Example I. After vortexing, the bacteriophage debris is eliminated from the solution by low speed centrifugation.

The resulting supernatant is transferred to a test tube having a 0.8 micron pore size cellulose acetate filter and a 5 ml receiver tube [Schliecher and Schuell]. 1.3 mls isopropanol is added to the tube and it is vortexed gently, followed by a 2 minute room temperature incubation. To bind the DNA to the filter, the contents of the tube are centrifuged for 4 minutes at 3000 rpm at room temperature. While the DNA is on the filter, 0.5 mls of 70% ethanol is added to the tube and centrifuged again for two minutes. This step is repeated three more times to insure complete removal of contaminants.

The receiver tube is then removed and replaced with a 1.5 ml, capless Eppendorf tube. 0.1 ml of a reagent solution containing 10 mM Tris-Cl at pH 8.0, 1 mM EDTA and 20 ugs/ml RNase A is added to the tube and incubated for 30 minutes at room temperature to allow the DNA to be released from the filter. The tube and its contents are then centrifuged for four minutes at 3000 rpm at room temperature.

0.5 ul of the resulting solution was employed in the Sanger dideoxy sequencing protocol. The solution containing DNA fragments is analyzed by gel electrophoresis, producing linearized single-stranded M13 DNA.

When the procedure described in Maniatis et al was applied to purify the same cultures employed in Examples II and III, the electrophoretic gel data produced the same results as did the method of the present invention. However, the time savings caused by use of the automated method of the present invention was approximately 10–15 percent. Additionally, in both the manual and automated DNA isolation procedures of the present invention resulted in significantly higher yields of the isolated DNA fragments.

Numerous modifications may be made by one skilled in the art to the methods and components of the present invention in view of the disclosure herein. Such modifications are believed to be encompassed in the appended claims.

We claim:
1. A method for isolating and purifying DNA molecules from cell culture medium of the type in which:
   (a) cells in the culture are concentrated apart from major contaminants in the media;
   (b) the cells are lysed and deproteinated;
   (c) cellular debris is eliminated;
   (d) the DNA is extracted by precipitation;
   (e) the DNA is washed to remove contaminants; and
   (f) the precipitated DNA is isolated by elution;
   wherein the improvement comprises performing said lysing and deproteinating in one step with a stable single phase aqueous reagent composition comprising:
   (i) about 1.6 to 3.2M potassium acetate;
   (ii) about 5 to 15% by weight phenol;
   (iii) about 5 to 15% by weight chloroform; and
   (iv) glacial acetic acid in an amount such that the weight ratio of potassium acetate to acetic acid is 3:2, wherein the weight ratio of (i) to the combination of (ii) and (iii) is in the range of 4:1 to 4:3.

2. The method according to claim 1 wherein DNA comprises double-stranded plasmid DNA or single-stranded bacteriophage DNA.

3. The method according to claim 2 wherein said bacteriophage is M13.

* * * * *